US012116621B2

(12) United States Patent
Cho (10) Patent No.: US 12,116,621 B2
(45) Date of Patent: Oct. 15, 2024

(54) METHOD OF DETECTING SMALL RNA

(71) Applicant: XENOHELIX CO., LTD, Jeonju-si (KR)

(72) Inventor: Seok Keun Cho, Incheon (KR)

(73) Assignee: XENOHELIX CO., LTD, Jeonju-si (KR)

( * ) Notice: Subject to any disclaimer, the term of this patent is extended or adjusted under 35 U.S.C. 154(b) by 0 days.

(21) Appl. No.: 17/104,336

(22) Filed: Nov. 25, 2020

(65) Prior Publication Data

US 2021/0198725 A1   Jul. 1, 2021

(30) Foreign Application Priority Data

Dec. 31, 2019 (KR) .................. 10-2019-0179664
May 8, 2020 (KR) .................. 10-2020-0055429

(51) Int. Cl.
*C12Q 1/68* (2018.01)
*C12Q 1/6825* (2018.01)

(52) U.S. Cl.
CPC ................ *C12Q 1/6825* (2013.01)

(58) Field of Classification Search
CPC ............ C12Q 1/6825; C12Q 2521/501; C12Q 2525/121; C12Q 2525/186; C12Q 2525/191; C12Q 2533/101; C12Q 2535/122; C12Q 2563/179; C12Q 2565/631

See application file for complete search history.

(56) References Cited

U.S. PATENT DOCUMENTS

2007/0077582 A1* 4/2007 Slepnev ............... C12Q 1/6851
                                                            435/6.16
2010/0316991 A1* 12/2010 Roth ........................ C12N 7/00
                                                            435/235.1
2014/0221228 A1  8/2014 Ginsberg et al.
2018/0163263 A1* 6/2018 Uemori .................... C12Q 1/68
2021/0017580 A1* 1/2021 Yang ..................... C12Q 1/686

FOREIGN PATENT DOCUMENTS

WO    2008/094980 A2    8/2008
WO    2020/213800 A1    10/2020

OTHER PUBLICATIONS

Cornelis Senne et al, Forensic SNP Genotyping using Nanopore MinION Sequencing, Feb. 3, 2017, Scientific Reports, vol. 7, No. 41759, pp. 1-5. , (Year: 2017).*
Wojciech, Makalowski et al., "Bioinformatics of nanopore sequencing", Journal of Human Genetics, dated Aug. 2019, 7 pages.
Office Action issued Jul. 16, 2021 in Korean Application No. 10-2020-0055429.
Extended European Search Report issued May 19, 2021 in European Application No. 20210024.4.
Dong et al., "Colorimetric PCR-Based microRNA Detection Method Based on Small Organic Dye and Single Enzyme", Analytical Chemistry, 2018, vol. 90, pp. 7107-7111 (5 pages total).
Goo et al., "Rolling Circle Amplification as Isothermal Gene Amplification in Molecular Diagnostics", BioChip J., 2016, vol. 10, No. 4, pp. 262-271 (10 pages total).
Cornelis et al., "Forensic SNP Genotyping using Nanopore MinION Sequencing", Scientific Reports, vol. 7, No. 41759, pp. 1-5 (5 pages total).
Jiang et al., "A Novel Design Combining Isothermal Exponential Amplification and Gold-Nanoparticles Visualization for Rapid Detection of MiRNAs", International Journal of Molecular Sciences, 2018, vol. 19, No. 3374, pp. 1-14 (14 pages total).
Office Action issued Dec. 1, 2022 in European Application No. 20 210 024.4.

* cited by examiner

Primary Examiner — Jehanne S Sitton
(74) Attorney, Agent, or Firm — Sughrue Mion, PLLC (57) ABSTRACT

The present invention relates to a method of analyzing and detecting small RNA. In particular, the present invention can also analyze even RNA having a short base sequence, and quantitatively detect the RNA with high sensitivity and accuracy, and thus can be widely used for diagnosis of various diseases such as infectious diseases and cancer.

7 Claims, 5 Drawing Sheets

Specification includes a Sequence Listing.

SEQUENCE LISTING

```
<160> NUMBER OF SEQ ID NOS: 14

<210> SEQ ID NO 1
<211> LENGTH: 22
<212> TYPE: RNA
<213> ORGANISM: Artificial Sequence
<220> FEATURE:
<223> OTHER INFORMATION: has-miR-21-5p

<400> SEQUENCE: 1
uagcuuauca gacugauguu ga                                              22

<210> SEQ ID NO 2
<211> LENGTH: 22
<212> TYPE: RNA
<213> ORGANISM: Artificial Sequence
<220> FEATURE:
<223> OTHER INFORMATION: has-miR-210-3p

<400> SEQUENCE: 2
cugugcgugu gacagcggcu ga                                              22
```

```
<210> SEQ ID NO 3
<211> LENGTH: 22
<212> TYPE: RNA
<213> ORGANISM: Artificial Sequence
<220> FEATURE:
<223> OTHER INFORMATION: has-miR-486-5p

<400> SEQUENCE: 3
uccuguacug agcugccccg ag                                              22

<210> SEQ ID NO 4
<211> LENGTH: 22
<212> TYPE: DNA
<213> ORGANISM: Artificial Sequence
<220> FEATURE:
<223> OTHER INFORMATION: sensing region of sensor DNA detecting for
      has-miR-486-5p

<400> SEQUENCE: 4
tcaacatcag tctgataagc ta                                              22

<210> SEQ ID NO 5
<211> LENGTH: 22
<212> TYPE: DNA
<213> ORGANISM: Artificial Sequence
<220> FEATURE:
<223> OTHER INFORMATION: sensing region of sensor DNA detecting for
      has-miR-210-3p

<400> SEQUENCE: 5
tcagccgctg tcacacgcac ag                                              22

<210> SEQ ID NO 6
<211> LENGTH: 22
<212> TYPE: DNA
<213> ORGANISM: Artificial Sequence
<220> FEATURE:
<223> OTHER INFORMATION: sensing region of sensor DNA detecting for
      has-miR-486-5p

<400> SEQUENCE: 6
ctcggggcag ctcagtacag ga                                              22

<210> SEQ ID NO 7
<211> LENGTH: 88
<212> TYPE: DNA
<213> ORGANISM: Artificial Sequence
<220> FEATURE:
<223> OTHER INFORMATION: module region of sensor DNA detecting for
      has-miR-21-5p

<400> SEQUENCE: 7
aacaatacca cgaccaccga caactacacg ctacagtcgc atacgagatc gtgatgtgac     60
tggagttgct tggctctggt gtattggt                                        88

<210> SEQ ID NO 8
<211> LENGTH: 88
<212> TYPE: DNA
<213> ORGANISM: Artificial Sequence
<220> FEATURE:
<223> OTHER INFORMATION: module region of sensor DNA detecting for
      has-miR-210-3p
```

<400> SEQUENCE: 8
aacaatacca cgaccaccga caactacacg ctacagtcgc atacgagata catcggtgac    60
tggagttgct tggctctggt gtattggt    88

<210> SEQ ID NO 9
<211> LENGTH: 88
<212> TYPE: DNA
<213> ORGANISM: Artificial Sequence
<220> FEATURE:
<223> OTHER INFORMATION: module region of sensor DNA detecting for
      has-miR-486-5p

<400> SEQUENCE: 9
aacaatacca cgaccaccga caactacacg ctacagtcgc atacgagatt taggcgtgac    60
tggagttgct tggctctggt gtattggt    88

<210> SEQ ID NO 10
<211> LENGTH: 6
<212> TYPE: DNA
<213> ORGANISM: Artificial Sequence
<220> FEATURE:
<223> OTHER INFORMATION: barcode region of sensor DNA detecting for
      has-miR-21-5p

<400> SEQUENCE: 10 cgtgat    6

<210> SEQ ID NO 11
<211> LENGTH: 6
<212> TYPE: DNA
<213> ORGANISM: Artificial Sequence
<220> FEATURE:
<223> OTHER INFORMATION: barcode region of sensor DNA detecting for
      has-miR-210-3p

<400> SEQUENCE: 11 acatcg    6

<210> SEQ ID NO 12
<211> LENGTH: 6
<212> TYPE: DNA
<213> ORGANISM: Artificial Sequence
<220> FEATURE:
<223> OTHER INFORMATION: barcode region of sensor DNA detecting for
      has-miR-486-5p

<400> SEQUENCE: 12 ttaggc    6

<210> SEQ ID NO 13
<211> LENGTH: 24
<212> TYPE: DNA
<213> ORGANISM: Artificial Sequence
<220> FEATURE:
<223> OTHER INFORMATION: Forward primer

<400> SEQUENCE: 13
aacaatacca cgaccaccga caac    24

<210> SEQ ID NO 14
<211> LENGTH: 24
<212> TYPE: DNA
<213> ORGANISM: Artificial Sequence
<220> FEATURE:

```
<223> OTHER INFORMATION: Reverse primer

<400> SEQUENCE: 14
accaatacac cagagccaag caac                                              24
```

METHOD OF DETECTING SMALL RNA

CROSS-REFERENCE TO RELATED APPLICATION

This application claims priority to and the benefit of Korean Patent Application No. 2019-0179664, filed on Dec. 31, 2019, and Korean Patent Application No. 2020-0055429, filed on May 8, 2020 the disclosure of which is incorporated herein by reference in its entirety.

TECHNICAL FIELD

The present invention relates to a method of analyzing and detecting small RNA. In particular, the present invention can analyze even RNA having a short base sequence, and quantitatively detect the RNA with high sensitivity and accuracy, and thus can be widely used for diagnosis of various diseases such as infectious diseases and cancer.

BACKGROUND ART

As the quality of life is improved, interest in early diagnosis of diseases has increased and because molecular diagnostic technology directly detects genetic information of a pathogen which causes a disease, the molecular diagnostic technology has been attracting much attention as a technology capable of solving the disadvantages of an immunological diagnostic technology which detects the indirect factors of a disease based on the existing antibody/antigen reaction.

Further, recently, as the coronavirus infection-19 (COVID-19) has been greatly spreading, the outbreak has caused many deaths worldwide, and the World Health Organization (WHO) even declared the outbreak a pandemic. In the case of diseases caused by such an RNA virus, a high mutation incidence causes more damage, and early diagnosis of whether a patient has been infected is further required.

Meanwhile, small RNA such as miRNA is protein-non-coding RNA which is present in vivo, and may act on the post-transcriptional process of a specific gene to regulate the expression of the corresponding gene. In particular, small RNA is recognized as an important genetic element which regulates biological functions such as cell cycle, differentiation, development, metabolism, carcinogenesis, and aging to mediate the homeostasis of an organism, and in particular, the formation of an abnormal network thereof may exhibit a fatal defect in terms of cell physiology.

Further, an expression pattern of small RNA such as miRNA in blood shows a strong advantage in early and predictive detection of cancer because the small RNA sensitively reacts in the early stage of cancer. In addition, since various cancers can be tested with simple blood sampling, the burden imposed on the body of a patient can be reduced. Furthermore, in the diagnosis of various intractable diseases such as Alzheimer's disease and Parkinson's disease in addition to the aforementioned infections and cancers, there is an increasing need for developing a technology capable of diagnosing the diseases early by rapidly detecting small RNA with high sensitivity.

DESCRIPTION OF EMBODIMENTS

Technical Problem

The technical problem to be solved by the present invention is to provide a method of detecting small RNA.

Also, the technical problem to be solved by the present invention is to provide a sensor DNA for detecting small RNA.

Technical Solution

According to an aspect of the present invention relates to a method of detecting small RNA, the method including: a) hybridizing sensor DNA including a complementary sequence of target small RNA to be detected with the target small RNA; b) performing polymerization with a polymerase using a module region of the sensor DNA as a template and the target small RNA as a primer; c) amplifying and producing an amplicon using the module region of the sensor DNA and a primer corresponding to a strand polymerized in step b); and d) analyzing a sequence of the amplicon.

In one embodiment, the sensor DNA may have a modified amine region at the 3' end. Such modification may prevent polymerization of the sensor DNA from occurring in the process of polymerization by the polymerase in step b). Accordingly, a modified form can be applied as long as it can prevent the polymerization of the sensor DNA, and the form is not limited.

In one embodiment, the primer in step c) may have a phosphate bound to the 5' end. The primer in step c) is used to produce an amplicon through an amplification reaction, and a base sequence of the primer can be applied without limitation as long as the base sequence can be bound to a strand to be amplified through the phosphate bound to the 5' end.

That is, the base sequence may be changed depending on the target small RNA to be detected or the module region of the sensor DNA.

In one embodiment, when a plurality of amplicons are produced in step c), the method may further include: d) ligating the produced amplicons.

Through the ligation, the base sequence of the small RNA may be analyzed even with the Oxford Nanopore sequencing system (Oxford Nano) in the related art, which cannot analyze short base sequences.

In one embodiment, after the ligation of the amplicons, the method may further include: attaching adenine (A) to the 3' end by adding a dATP and a DNA polymerase thereto, and as the DNA polymerase, a Taq polymerase may be used, but the present invention is not limited thereto.

In one embodiment, step d) may additionally include: after ligation of amplicons, binding an adaptor for sequencing to both ends of the ligated amplicons. The adaptor is capable of being recognized by a sequencing device, and may be bound by changing the adaptor depending on a sequencing device to be applied, such as an Oxford Nanopore sequencing device and a next generation sequencing (NGS) device.

In one embodiment, the method may further include: analyzing a sequence of the ligated amplicons after step d). In step c), the sequencing may be Nanopore sequencing.

The nanopore sequencing may mean typical 'nanopore sequencing'. The 'nanopore sequencing' refers to a technique for discriminating various bases by measuring the difference in electrical conductivity while passing a strand of DNA through a biological pore. Since the nanopore sequencing analyzes a base sequence while passing the sequence through pores, the nanopore sequencing has a disadvantage in that a short base sequence cannot be analyzed, and thus cannot be applied to the detection and analysis of small RNA.

The present invention enables small RNA to be detected and analyzed by ligating amplicons to provide a level of length which can be analyzed even through the nanopore sequencing. Furthermore, the present invention may be applied without limitation to a sequencing technique.

In one embodiment, the sensor DNA may include a unique barcode region. The barcode region is unique according to the type of target small RNA, and may correspond to the presence and number of target small RNAs by confirming the presence of the barcode region and the number of barcodes to be detected.

In one embodiment, the amplicon may be amplified by including a barcode region of the sensor DNA. When a unique barcode region different from the type of target small RNA is present in the sensor DNA, each ampicon produced during the process in which the amplicon is amplified and produced may be an amplicon in which a unique barcode region included in all sensor DNAs is included.

In one embodiment, the 'detection' may be capable of quantitatively detecting up to the number of target small RNAs by measuring the number of amplicons.

In one embodiment, the number of amplicons may be confirmed by measuring the number of barcodes included in the amplicons.

Figure 6:
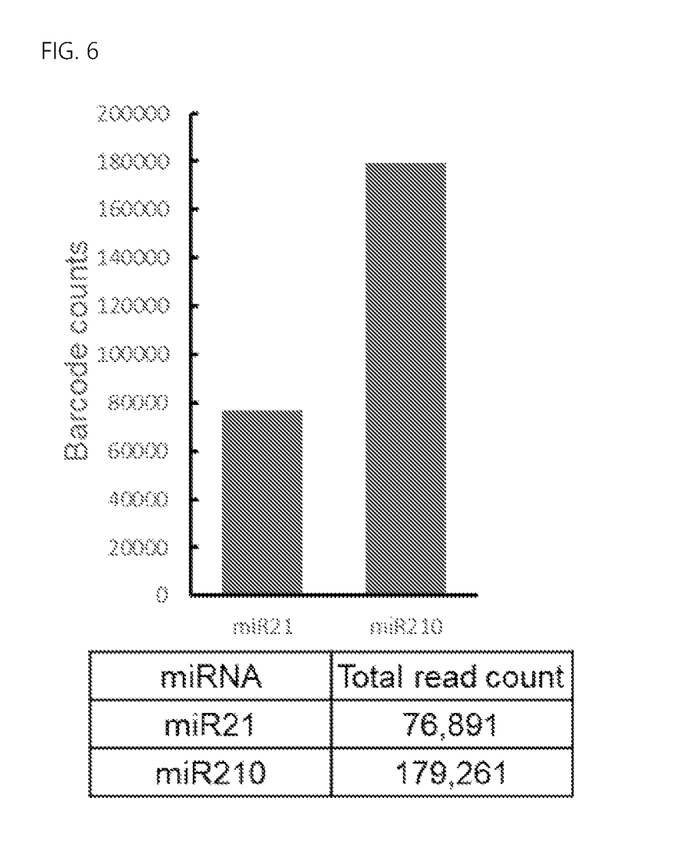
FIG. 6 illustrates the results of confirming the quantitative detection ability when multiple sensors are mixed for multiple small RNAs.
Figure 7:
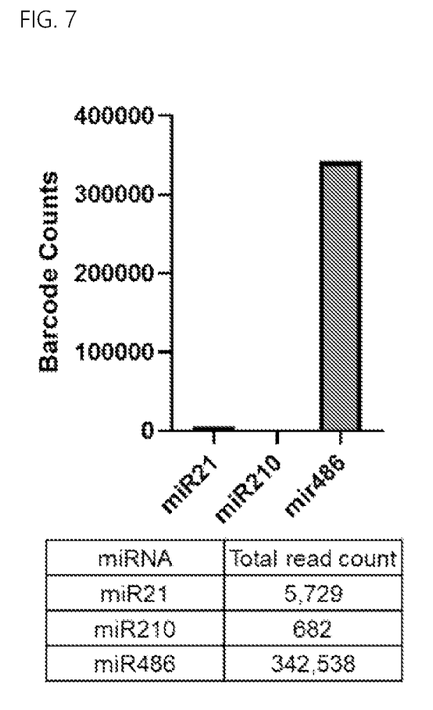
FIG. 7 illustrates the results of confirming the quantitative detection ability of the target small RNA in an RNA sample extracted from blood.

In an exemplary embodiment of the present invention, it was confirmed that a quantitative number of target small RNAs could be detected with high accuracy and sensitivity even when multiple sensors for multiple target small RNAs are mixed (FIG. 6), and furthermore, it was confirmed that a quantitative number of target small RNAs could be detected with high accuracy and sensitivity by introducing sensor DNA for target small RNA to be confirmed even in an RNA sample extracted from blood (FIG. 7).

In particular, the method of detecting small RNA of the present invention and the configuration of the sensor DNA used for detection have very low detection limits at the femtomolar (fmol) and attomolar (amol) levels, and thus show that both sensitivity and accuracy are remarkably excellent compared to those of the small RNA detection technique in the related art.

Another aspect of the present invention relates to sensor DNA for detecting small RNA in which a) a small RNA sensing region including a complementary sequence of target small RNA; b) a module region which is a template such that polymerization can be performed using the sensed target small RNA as a primer; and c) an amine region at the 3' end; are modified.

In one embodiment, the module region may include a unique barcode region. The 'barcode region' is as described above.

In one embodiment, the sensor may be a nanopore sensor. The 'nanopore sensor' is a nanopore-based sensor, and means that nanopore sequencing may be applied.

Advantageous Effects of Invention

The method of detecting small RNA of the present invention and the configuration of the sensor DNA used for detection have very low detection limits at the femtomol (fmol) and atomol (amol) levels, and both sensitivity and accuracy are remarkably excellent compared to those of the small RNA detection technique in the related art.

Accordingly, the present invention can be effectively utilized even for diagnosis at the very early stage and latent stage of a disease by enabling molecular diagnosis at a fine level to overcome the detection limits of existing technology, such as diagnosis of whether a disease occurs in an individual such as a human, what stage has the disease progressed to, and whether the individual is infected with a virus at the latent stage.

The effect of the present invention is not limited to the aforementioned effects, and it should be understood to include all possible effects deduced from the configuration of the invention described in the detailed description or the claims of the present invention.

DETAILED DESCRIPTION OF EXEMPLARY EMBODIMENTS

Hereinafter, the present invention will be described in detail through the Examples. However, the following Examples are only for exemplifying the present invention, and the present invention is not limited by the following Examples.

Example 1. Polymerization, Amplification and Sequencing Using Sensor DNA

After small RNA as a target and sensor DNA were added, a polymerization reaction was performed at 95° C. for 30 seconds and 63° C. for 10 minutes using a DNA polymerase (XenoT-POL). Thereafter, the sensor and the RNA were digested using an endonuclease. The sensor DNA includes a sensing region including a sequence complementary to the target small RNA, and the sensing region senses the target small RNA and hybridizes with the target small RNA, and is named 'sensor DNA' in the present invention. The sensor DNA may include a barcode region, and the number of target small RNAs may be quantitatively measured by counting only the barcode region.

Thereafter, amplicon(s) was(were) produced by PCR using a primer having a phosphate bound to the 5' end for amplification of the module region of the sensor DNA and the polymerized strand. The PCR may be performed in the same manner as in typical PCR, and the temperature conditions, cycle number, and the like of the PCR may be appropriately modified and applied depending on the polymerized strand and a sequence of a primer bound to the polymerized strand.

Thereafter, after the produced amplicons were ligated using a DNA ligase, the ligated amplicons were subjected to sequencing.

The sensor DNA is a nanopore-based sensor, and sequencing (nanopore sequencing) using a nanopore may be applied to the sequencing. Specifically, after a nanopore adaptor is bound to the ligated amplicons, nanopore sequencing may be performed, and the nanopore sequencing may be performed according to a manual of a known product using the known product. For example, after a sample is loaded onto a Minion chip which is a nanopore sequencing device, the sequencing may be performed.

The accuracy and sensitivity of the detection method of the present invention was confirmed by the following experimental examples, and experiments were exemplarily performed using miRNA21, miRNA210, and miRNA486 as targets. A sequence of the target miRNA is as summarized in the following Table 1.

TABLE 1

| SEQ ID NO | Type of target miRNA | Sequence of target miRNA |
|---|---|---|
| 1 | hsa-miR-21-5p | UAGCUUAUCAGACUGAUGUUGA |
| 2 | hsa-miR-210-3p | CUGUGCGUGUGACAGCGGCUGA |
| 3 | hsa-miR-486-5p | UCCUGUACUGAGCUGCCCCGAG |

A sequence of a sensing region of sensor DNA for detecting the exemplary target miRNA is as summarized in the following Table 2. The sequence of the present sensing region may be modified if necessary, and is not limited to the present example.

TABLE 2

| SEQ ID NO | Type of target miRNA | Sequence (5'-3') of sensing region of sensor DNA |
|---|---|---|
| 4 | hsa-mi4-21-5p | TCAACATCAGTCTGATAAGCTA |
| 5 | has-miR-210-3p | TCAGCCGCTGTCACACGCACAG |
| 6 | hsa-miR-486-5p | CTGGGGCAGCTCAGTACAGGA |

A sequence of a module region of sensor DNA for detecting the exemplary target miRNA is as summarized in the following Table 3. A sequence of a barcode region included in the module region is underlined. The sequence of the present module region may be modified if necessary, and is not limited to the present example.

TABLE 3

| SEQ ID NO | Type of target miRNA | Sequence (5'-3') of module region of sensor DNA |
|---|---|---|
| 7 | hsa-miR-21-5p | AACAATACCACGACCACCGACAACTACACGCTACAG TCGCATACGAGATCGTGATGTGACTGGAGTTGCTTG GCTCTGG TGTATTGGT |
| 8 | hsa-miR-210-3p | AACAATACCACGACCACCGACAACTACACGCTACAG TCGCATACGAGATACATCGGTGACT GGAGTTGCTT GGCTCTGG TGTATTGGT |
| 9 | hsa-miR-486-5p | AACAATACCACGACCACCGACAACTACACGCTACAG TCGCATACGAGATTTAGGCGTGACT GGAGTTGCTT GGCTCTGG TGTATTGGT |

A sequence of a barcode region of sensor DNA for detecting the exemplary target miRNA is as summarized in the following Table 4. The sequence of the present barcode region may be modified if necessary, and is not limited to the present example.

TABLE 4

| SEQ ID NO | Type of target miRNA | Sequence (5'-3') of barcode region of sensor DNA |
|---|---|---|
| 10 | hsa-miR-21-5p | CGTGAT |
| 11 | hsa-miR-210-3p | ACATCG |
| 12 | hsa-miR-486-5p | TTAGGC |

As the module region includes the barcode region and is connected to the sensing region as described above, the module region can be classified by the sensing region and/or the barcode region.

In addition, exemplarily, a sequence of a primer having a phosphate bound to the 5' end used for amplification of a module region of sensor DNA and a polymerized strand is as follows. The present primer is only characterized as having a phosphate bound to the 5' end, and a sequence of the primer may be modified if necessary, and is not limited to the present example.

TABLE 5

| SEQ ID NO | Type of primer | Sequence (5'-3') of primer |
|---|---|---|
| 13 | Forward primer | [phosphate]AACAATACCACGACCACCGACAAC |
| 14 | Reverse primer | [phosphate]ACCAATACACCAGAGCCAAGCAAC |

Experimental Example 1. Confirmation of Accuracy of Small RNA Detection Technique Using Sensor DNA of Present Invention (when Sensor DNA is Mixed)

Ater 20 fmol of miR210 as target small RNA and 20 fmol of each of Sensor 21 (sensor DNA including an miRNA21 sensing region) and Sensor 210 (sensor DNA including an miR210 sensing region) were mixed, it was confirmed whether target miRNA was accurately detected even in a state in which various types of sensor DNAs were mixed using the method in Example 1.

First, after Sensor 21 and Sensor 210 each at a concentration of 20 fmol were suitably mixed under experimental conditions, 2 μl of a reaction buffer (200 mM Tris-HCl, 100 mM (NH$_4$)$_2$SO$_4$, 100 mM KCl, 20 mM MgSO$_4$, 1% Triton X-100, and (pH 8.8 at 25° C.)), 1 μl of 10 mM dNTP, and 2 units of XenoT-POL were added thereto, and then the resulting mixture was heated at 95° C. for 30 seconds, and then incubated at 63° C. for 10 minutes. A reaction sample was cleaned up using the MEGAquick-spin™ Plus Total Fragment DNA Purification Kit, and eluted with 60 µl of distilled water. 20 µl of the sample was mixed with a nuclease mixture (40 mM sodium acetate, pH 4.5 at 25° C.), 3M mM NaCl, 2 mM $ZnSO_4$ and 200 units of an S1 nuclease)), and the resulting mixture was incubated at 37° C. for 11 minutes. Thereafter, the mixture was cleaned up using the MEGAquick-spin™Plus Total Fragment DNA Purification Kit, and eluted with 60 µl of distilled water. PCR was performed under conditions of one cycle of 98° C. for 2 minutes and 30 cycles of 98° C. for 10 seconds and 64.5° C. for 10 seconds using primers having a phosphate bound to the 5' end. After a PCR product was electrophoresed on a 15% polyacrylamide gel (19:1), the results were confirmed using Gel Doc.

Figure 1:
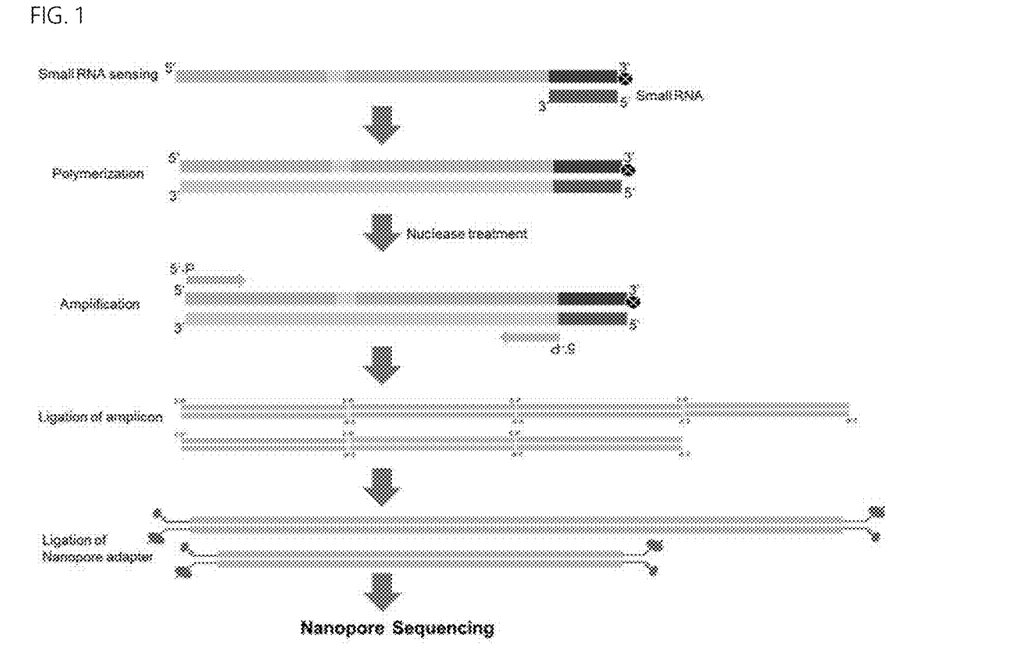
FIG. 1 illustrates a schematic view of a method of detecting small RNA according to an exemplary embodiment of the present invention. After sensor DNA senses and binds to target small RNA, sequencing for detecting the small RNA is performed.
Figure 2:
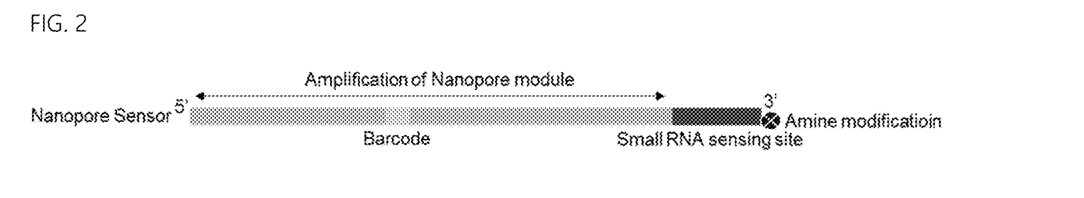
FIG. 2 illustrates a structural view of sensor DNA according to an exemplary embodiment of the present invention.
Figure 3:
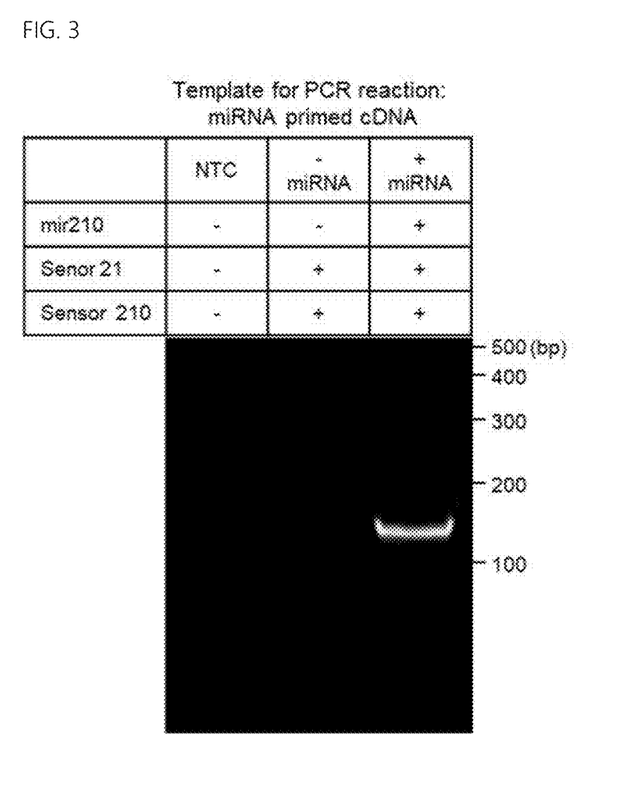
FIG. 3 illustrates the results of confirming that miR210, which is an exemplary detection target, is accurately detected using the sensor of the present invention.

As a result, as illustrated in FIG. 3, it was confirmed that even when sensor DNA which does not correspond to target small RNA was mixed, miRNA210, which is the target small RNA, could be accurately sensed and detected by Sensor 210, and it was confirmed that a non-specific reaction with Sensor 21 did not appear.

These results show that a small RNA detection technique using the sensor DNA of the present invention can maintain accuracy even when various types of sensors are mixed.

Experimental Example 2. Confirmation of Sensitivity of Small RNA Detection Technique Using Sensor DNA of Present Invention in Blood Sample RNA was purified and extracted from a human blood sample using an miRNeasy serum/plasma kit (Qiagen). It was confirmed whether target miRNA was accurately detected using the method of Example 1.

Specifically, after 800 ng of RNA purified from blood was mixed with 200 amol of each of Sensor 21, Sensor 210 and Sensor 486 (sensor DNA including an miRNA486 sensing region), 2 µl of a reaction buffer (200 mM Tris-HCl, 100 mM $(NH_4)_2SO_4$, 100 mM KCl, 20 mM $MgSO_4$, 1% Triton X-100, (pH 8.8 at 25° C.)), 1 µl of 10 mM dNTP, and 2 units of XenoT-POL were added thereto, and then the resulting mixture was heated at 95° C. for 30 seconds, and then incubated at 63° C. for 10 minutes. A reaction sample was cleaned up using the MEGAquick-spin™Plus Total Fragment DNA Purification Kit, and eluted with 60 µl of distilled water. 20 µl of the sample was added to a nuclease mixture (40 mM sodium acetate, pH 4.5 at 25° C., 300 mM NaCl, 2 mM $ZnSO_4$ and 200 units of an S nuclease), and the resulting mixture was incubated at 37° C. for 11 minutes. Thereafter, the mixture was cleaned up using the MEGAquick-spin™Plus Total Fragment DNA Purification Kit, and eluted with 60 µl of distilled water. PCR was performed under conditions of one cycle of 98° C. for 2 minutes and 30 cycles of 98° C. for 10 seconds and 64.5° C. for 10 seconds using primers having a phosphate bound to the 5' end. After a PCR product was electrophoresed on a 15% polyacrylamide gel (19:1), the results were confirmed using Gel Doc.

Figure 4:
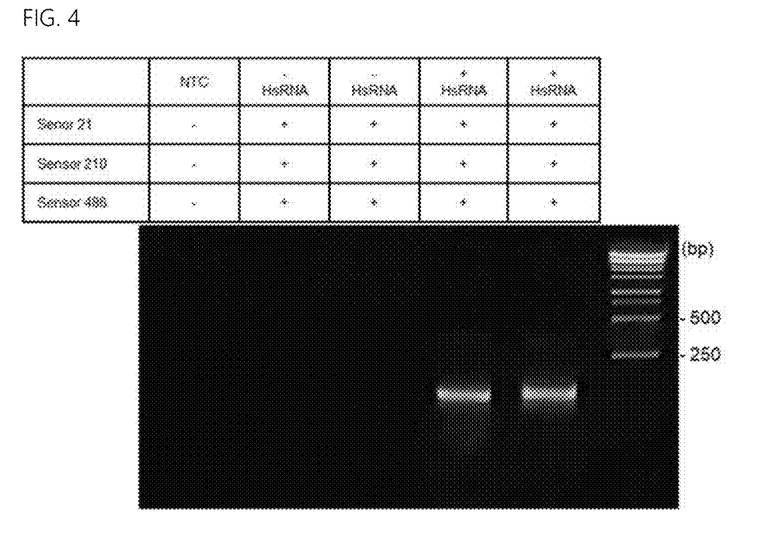
FIG. 4 illustrates the results of confirming the sensitivity of a small RNA detection technique using the sensor DNA of the present invention in a blood sample.

As a result, as illustrated in FIG. 4, it was confirmed that small RNA could be sensed when present even though the concentration of the sensor was remarkably low as 200 amol, so that it was confirmed that the detection limit was very low and high sensitivity could be exhibited.

Experimental Example 3. Confirmation of Quantitative Detection Activity of Small RNA Detection Technique Using Sensor DNA of Present Invention 3-1. Confirmation of Quantitative Detection Ability when Multiple Sensors for One Type of Target Small RNA are Mixed After 20 fmol of miRNA21 as target small RNA and 20 fmol of each of Sensor 21 and Sensor 210 were mixed, it was verified whether the detection of target miRNA could be quantitatively confirmed even in a state where various types of sensor DNAs were mixed using the method of Example 1. After 20 fmol each of Sensor 21, Sensor 210 and miRNA21 were suitably mixed under experimental conditions, 2 µl of a reaction buffer (200 mM Tris-HCl, 100 mM $(NH_4)_2SO_4$, 100 mM KCl, 20 mM $MgSO_4$, 1% Triton X-100, and (pH 8.8 at 25° C.)), 1 µl of 10 mM dNTP, and 2 units of XenoT-POL were added thereto, and then the resulting mixture was heated at 95° C. for 30 seconds, and then incubated at 63° C. for 10 minutes. A reaction sample was cleaned up using the MEGAquick-spin™Plus Total Fragment DNA Purification Kit, and eluted with 60 µl of distilled water. 20 µl of the sample was added to a nuclease mixture (40 mM sodium acetate, pH 4.5 at 25° C., 300 mM NaCl, 2 mM $ZnSO_4$ and 200 units of an S1 nuclease), and the resulting mixture was incubated at 37° C. for 11 minutes. Thereafter, the mixture was cleaned up using the MEGAquick-spin™Plus Total Fragment DNA Purification Kit, and eluted with 60 µl of distilled water. PCR was performed under conditions of one cycle of 98° C. for 2 minutes and 30 cycles of 98° C. for 10 seconds and 64.5° C. for 10 second using primers having a phosphate bound to the 5' end, and the amplicons were cleaned up. Thereafter, after SM units of a T3 DNA ligase was added to S00 ng of the amplicons under conditions of 66 mM Tris-HCl, 10 mM $MgCl_2$, 1 mM ATP, 1 mM DTT, and 7.5% polyethylene glycol (PEG 6000) (pH 7.6 at 25° C.), the resulting mixture was incubated at 25° C. for 10 minutes. Thereafter, after the mixture was cleaned up, 50 µl of a mixture was produced by mixing 40 µl of the eluted DNA, 1 µl of 1 mM dATP, 1 ul (5 units) of a taq DNA polymerase, 5 µl of a reaction buffer (200 mM Tris-HCl/pH 8.8), 500 mM KCl, 25 mM $MgCl_2$, 100 mM β-Mercaptoethanol and distilled water, and then incubated at 72° C. for 20 minutes. A dATP tailed DNA product was cleaned up using the MEGAquick-spin™ Plus Total Fragment DNA Purification Kit. Thereafter, processes of adaptor ligation (SQK-LSK109) for nanopore sequencing, clean-up using AMPure XP beads, priming the flow cell, and loading the flow cell were performed according to a nanopore sequencing protocol. Thereafter, a detection result was confirmed by counting barcode region sequences of Sensor 21 and Sensor 210 in the obtained nanopore sequencing file.

Figure 5:
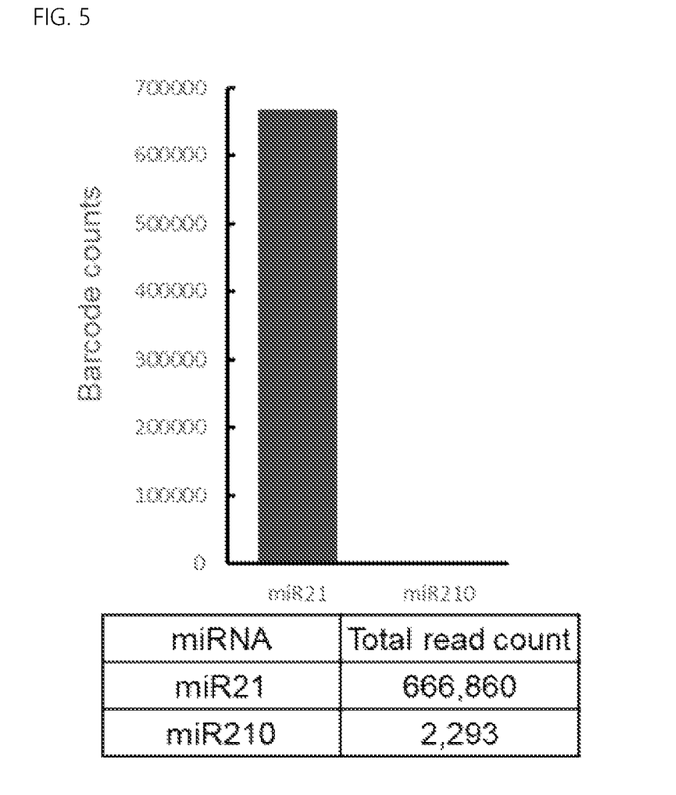
FIG. 5 illustrates the results of confirming the quantitative detection ability when multiple sensors are mixed for one type of target small RNA.

As a result, as illustrated in FIG. 5, as a result of counting the barcode regions of the sensor DNAs, 666,860 miRNA21s were measured, and it was confirmed that 2,293 miRNA210s appeared as the background.

The aforementioned results show that the technique of the present invention can measure the number of target small RNAs with high sensitivity and accuracy even at an extremely low concentration of femtomol (fmol) and quantitatively detect the target small RNAs.

3-2. Confirmation of Quantitative Detection Ability when Multiple Sensors for Multiple Target Small RNAs are Mixed miRNA21 and miRNA210, as target RNAs, were mixed at different concentrations of 7 fmol and 20 fmol, respectively, and 20 fmol each of Sensor21 and Sensor210 were mixed. Thereafter, it was verified whether the detection of the target miRNA could be quantitatively confirmed even in a state in which various types of sensor DNAs are mixed along with multiple target small RNAs using the method of Example 1.

20 fmol each of Sensor 21 and Sensor 210 were mixed with 7 fmol of miRNA21 and 20 fmol of miRNA210, and the process of the following nanopore sequencing is the same as that described in 3-1. Thereafter, a detection result was confirmed by counting barcode region sequences of Sensor 21 and Sensor 210 in the obtained nanopore sequencing file.

As a result, as illustrated in FIG. 6, in the case of miRNA21 mixed at a relatively low concentration of 7 fmol, 76,891 miRNA21s were measured, and in the case of miRNA210 mixed at a concentration of 20 fmol, 179,261 miRNA210s were measured.

The aforementioned results show that even when small RNAs are present at different concentrations, the technique of the present invention enables quantitative detection by reflecting the concentration or content included in the sample rather than simply detecting only the presence or absence thereof.

3-3. Confirmation Quantitative Detection Ability of Target Small RNA in RNA Sample Extracted from Blood RNA was purified and extracted from a human blood sample using an miRNeasy serum/plasma kit (Qiagen).

800 ng of the RNA purified from blood was mixed with 200 amol each of Sensor 21, Sensor 210, and Sensor 486, and thereafter, it was verified whether the detection of the target miRNA could be quantitatively confirmed using the method of Example 1. The process of the following nanopore sequencing is the same as that described in 3-1. Thereafter, a detection result was confirmed by counting barcode region sequences of Sensor 21, Sensor 210 and Sensor 486 in the obtained nanopore sequencing file.

As a result, as illustrated in FIG. 7, 5,279 miRNA21s, 682 miR210s, and 342,538 miRNA486s were measured depending on the concentration of each type of miRNA present in the blood.

The aforementioned results show that the technique of the present invention can rapidly diagnose the normal stage, the stage when a disease is developed, the latent stage, the onset stage, and the like at a molecular level as the presence of the small RNA which is an index for infections caused by viruses, bacteria, and the like, cancers, and the like is measured at a quantitative level rather than a simple detection thereof.

In particular, the method of detecting small RNA of the present invention and the configuration of the sensor DNA used for detection have very low detection limits at the femtomolar (fmol) and attomolar (amol) levels, and thus show that both sensitivity and accuracy are remarkably excellent compared to those of the small RNA detection technique in the related art.

As described above, the present invention can be applied even to diagnosis at the very early stage and latent stage of a disease by enabling molecular diagnosis at a fine level to overcome the detection limits of an existing technology, such as diagnosis of whether a disease occurs in an individual such as human, what stage the disease progresses to, and whether the individual is infected with a virus at the latent stage.

The above-described description of the present invention is provided for illustrative purposes, and those skilled in the art to which the present invention pertains will understand that the present invention can be easily modified into other specific forms without changing the technical spirit or essential features of the present invention.

Therefore, it should be understood that the above-described embodiments are only exemplary in all aspects and are not restrictive. For example, each constituent element which is described as a singular form may be implemented in a distributed form, and similarly, constituent elements which are described as being distributed may be implemented in a combined form.

The scope of the present invention is represented by the claims to be described below, and it should be interpreted that the meaning and scope of the claims and all the changes or modified forms derived from the equivalent concepts thereof fall within the scope of the present invention.

What is claimed is:

1. A method of detecting small RNA, the method comprising:
   a) hybridizing sensor DNA comprising a complementary sequence of target small RNA to be detected with the target small RNA, the sensor DNA comprising a unique barcode region different from a region of target small RNA recognition;
   b) performing polymerization with a polymerase using a module region of the sensor DNA as a template and the target small RNA as a primer;
   c) amplifying and producing a plurality of amplicons using the module region of the sensor DNA and a primer complementary to a strand polymerized in step b);
   c') ligating the produced amplicons; and
   d) analyzing a sequence of the plurality of amplicons, and identifying and counting the target small RNA that indicates the presence and number of the target small RNA by identifying and counting the unique barcode region,
   wherein the sensor DNA is in an amount of 200 amol to 20 fmol.

2. The method of claim 1, wherein the sensor DNA has a modified amine region at the 3' end.

3. The method of claim 1, wherein the primer in step c) has a phosphate bound to the 5' end.

4. The method of claim 1, wherein step c') further comprises binding an adaptor for sequencing to both ends of the ligated amplicons.

5. The method of claim 4, further comprising: e) analyzing a sequence of the ligated amplicons after step d).

6. The method of claim 5, wherein step e) comprises a nanopore sequencing.

7. The method of claim 1, further comprising quantitatively detecting a number of target small RNAs by measuring a number of amplicons.

* * * * *